United States Patent [19]

Kiefer et al.

[11] Patent Number: 5,128,151
[45] Date of Patent: Jul. 7, 1992

[54] STABILIZED MENADIONE BISULFITE FORMULATIONS AND THEIR PREPARATION

[75] Inventors: Hans Kiefer, Wachenheim; Wolfgang Buehler, Hockenheim; Joachim U. Schneider, Weisenheim; Hagen Jaedicke, Ludwigshafen, all of Fed. Rep. of Germany

[73] Assignee: Basf Aktiengesellschaft, Ludwigshafen, Fed. Rep. of Germany

[21] Appl. No.: 141,637

[22] Filed: Jan. 7, 1988

[30] Foreign Application Priority Data

Jan. 14, 1987 [DE] Fed. Rep. of Germany ....... 3700812

[51] Int. Cl.$^5$ ................ A61K 33/42; A61K 31/12; A61K 31/19
[52] U.S. Cl. .................. 424/602; 424/606; 514/557; 514/574; 514/681; 514/970
[58] Field of Search ............ 424/602, 606; 514/681, 514/557, 574, 970

[56] References Cited

U.S. PATENT DOCUMENTS

| | | | |
|---|---|---|---|
| 2,808,361 | 10/1957 | Barouset | 514/681 |
| 3,079,261 | 2/1963 | Berrati | 514/681 |
| 4,533,674 | 8/1985 | Schmidt et al. | 514/474 |
| 4,577,019 | 3/1986 | Bruschi | 546/316 |
| 4,735,969 | 4/1988 | Schneider et al. | 514/681 |
| 4,740,373 | 4/1988 | Kesselman et al. | 514/681 |

FOREIGN PATENT DOCUMENTS 1202624 10/1961 Fed. Rep. of Germany .
2855851 3/1986 Fed. Rep. of Germany .

OTHER PUBLICATIONS

Chem. Abst. 68:84377t(1968)–Olinescu et al.
Chem. Abst. 80:19618f(1974)–Lukovskaya et al.
Chem. Abst. 93:210268q(1980)–Uehara et al.
Chem. Abst. 97:184,052a(1982)–Makavou et al.
Chem. Abst. 101:60,157v(1984)–Kovacs et al.
Remington's Pharmaceutical Sciences 15th ed. (1975) pp. 1576–1588.

Primary Examiner—Frederick E. Waddell
Assistant Examiner—Raymond J. Henley, III
Attorney, Agent, or Firm—Keil & Weinkauf

[57] ABSTRACT

Powdered and/or granulated menadione sodium bisulfite formulations additionally contain a physiologically tolerated organic or inorganic acid.

The novel formulations possess good water solubility and stability.

16 Claims, No Drawings

STABILIZED MENADIONE BISULFITE FORMULATIONS AND THEIR PREPARATION

The present invention relates to stabilized menadione bisulfite formulations and processes for their preparation.

2-methyl-1,4-naphthoquinone (menadione), which is one of the vitamins of the K series, is known to possess high antihemorrhagic activity. In the literature, menadione is predominantly referred to as vitamin $K_3$ (cf. Ullmanns Encyklopädie der technischen Chemie, 4th Edition, Volume 23, page 649 et seq., Verlag Chemie, Weinheim, 1983).

In spite of the excellent antihemorrhagic activity of menadione, this product in its pure form has not become very important either in human medicine or in animal nutrition. The reasons for this are the insolubility of menadione in water, its low stability to environmental influences (heat, light) and the skin-irritant and inflammatory properties.

Derivatives whose antihemorrhagic activity is just as good as that of menadione and which have the disadvantages described to a lesser extent, if at all, are the addition compounds of alkali metal or alkaline earth metal bisulfites with menadione (cf., inter alia, German Published Application DAS 1,033,017, FR 996 080, U.S. Pat. No. 2,331,808, GB 771 180). These derivatives, for example the adduct of sodium bisulfite with menadione, which are generally referred to as MSB (menadione sodium bisulfites), have attained considerable commercial importance in the animal feed industry.

Scientific investigations (cf. M. Carmack, M. B. Moore and M. E. Balis, J. Amer. Chem. Soc. 72, 844–847 and J. C. Vire, G. J. Patrlavche and G. D. Christian, Anal. Chem. 51 (1979), 752 et seq.) and experience in the animal feed industry (J. Nir, J. Kafvi and R. Cohen, Poultry Science 57 (1978), 206–209) show that even MSB, the most commonly used bisulfite adduct, is not sufficiently stable to light, heat and moisture.

For this reason, attempts have been made to increase the stability of MSB by reacting it with suitable salts of weak bases in order to convert it into more poorly water-soluble products.

Among these compounds, menadione pyrimidinol bisulfite (MPB) is the most widely used one (cf. U.S. Pat. No. 3,328,169). This adduct contains menadione in an amount of 45.6%, but also contains 32.6% of dimethylpyrimidinol. However, the higher stability which this compound is actually found to possess is achieved by the presence of an exogenous substance and an intentional lower water solubility.

Because it is desirable to convert menadione into a readily water-soluble derivative, these derivatives accordingly constitute a backward step.

According to German Laid-Open Application DOS 2,855,851, an attempt has therefore been made to replace the stabilizing effect of the exogenous dimethylpyrimidinol by certain vitamins, such as vitamin $B_1$ or $B_5$ (nicotinic acid or nicotinamide). These vitamin adducts are certainly safe from the physiological point of view but still have the following disadvantages.

The compounds stated in German Laid-Open Application DOS 2,855,851 possess not only antihemorrhagic activity but also pronounced activity of the vitamin used for stabilization (cf. German Laid-Open Application DOS 2,855,851, page 8, paragraph 3). Both activities are inseparably combined in these compounds. For example, if it is intended to administer the adduct of menadionesulfonic acid with nicotinic acid for the prevention or alleviation of hemorrhage, the nicotinic acid, which has a completely different physiological activity, is inevitably also administered.

It is an object of the present invention to provide an antihemorrhagic product which has the advantageous activity of MSB but not the disadvantageous application properties of the stabilized derivatives described above.

We have found, surprisingly, that this object is achieved by the active compound MSB itself. For this purpose, it is merely necessary to combine the commercial, finely crystalline MSB with a physiologically tolerated organic or inorganic acid and to convert the product to a dry form.

According to the invention, it is possible to prepare very stable formulations using two variants.

A. In the first variant, the proposed formulations have a relatively high menadione sodium bisulfite content of from 90 to 99% by weight and additionally contain from 1 to 10% by weight of a physiologically tolerated organic or inorganic acid, the percentages in each case being based on the formulation.

These formulations are preferably obtained by spray-drying an aqueous solution of menadione sodium bisulfite and adding small amounts of a physiologically tolerated organic or inorganic acid by the fluidized bed or granulation method.

In spray-drying by the fluidized bed method, the solution or suspension is sprayed continuously or batchwise into a fluidized bed of product. The apparatus is provided with suitable means which make it possible to obtain a certain particle size fraction and to maintain the granulation process (K. Kröll, Trocknungstechnik, Volume II: Trockner und Trocknungsverfahren, 2nd Edition, Springer Verlag, Berlin 1978). In spray-drying by the granulation method, the solution or suspension is sprayed into a suitable spray tower and dried.

It is not possible to formulate a solution of menadione sodium bisulfite without the addition of the acid.

Thus, the added acids have a dual function. On the one hand, they increase the stability of the resulting formulations and on the other hand it is only through their presence that the spray granulation process is possible.

Suitable acids are primarily the products mentioned in West German animal feed legislation, e.g. fumaric acid, sorbic acid, citric acid, lactic acid, phosphoric acid, primary calcium phosphate and in particular tartaric acid.

In comparison with the known stabilized products, the novel formulations have the following advantages:
1. higher stability,
2. virtually the same menadione content as menadione sodium bisulfite,
3. simpler to handle since the products have a low dust content and are very free-flowing,
4. equally good water solubility as unformulated menadione sodium bisulfite, and hence very good bioavailability,
5. lower production costs compared with the previously known formulations and
6. no contamination with equimolecular chemical stabilizers, such as dimethylpyrimidinol.

B. In the second variant of the invention, the powdered menadione sodium bisulfite formulations proposed have a content of from 50 to 80% by weight of menadione sodium bisulfite, from 1 to 20% by weight of a physiologically tolerated organic or inorganic acid and from 1 to 49% by weight of a thickener, the percentages in each case being based on the formulations.

These formulations are advantageously obtained by drying or spraying and drying, in a fluidized bed, a concentrated aqueous solution or suspension of menadione sodium bisulfite, a physiologically tolerated organic or inorganic acid and a thickener or binder.

Suitable acids are the acids mentioned under A).

Examples of thickeners or binders are carbohydrates, such as starch or starch derivatives, and dextrins or proteins, such as gelatine. These substances both increase the viscosity in the range which is advantageous for spraying and serve as a cement which holds together the particles of active compound in the dry form in fairly large agglomerates, which, because they are free-flowing and have a low dust content, possess advantageous properties in use.

The solutions or suspensions can be dried in a thin layer on metal sheets or in suitable vessels; the desired free-flowing powders are particularly advantageously formed by spraying and drying in a fluidized bed. The amount of acid can vary within wide limits and is preferably from 5 to 50, particularly advantageously from 10 to 30, parts per 100 parts of menadione sodium bisulfite. The thickeners are added in an amount of from 10 to 100, preferably from 50 to 80, parts per 100 parts of menadione sodium bisulfite.

Compared to the known stabilized products, the novel formulations have the following advantages:
1. higher stability,
2. no contamination with equimolecular stabilization factors, such as dimethylpyrimidinol and
3. easier to handle since the products do not form dust.

VARIANT A

Preparation Examples

A1. A concentrated aqueous solution of 30 parts of MSB, as the bishydrate, 0.6 part of citric acid and 69.4 parts of water at 20° C. were sprayed via a nozzle into a fluidized bed consisting of MSB particles having a mean size of 1–4 μm. At intervals of 1 hour, the content of the fluidized bed was sieved and the particles having a size of 125–250 μm ($\approx$60% of the fluidized bed) were isolated. The fluidized bed was fed with a gas stream at 90° C., the outlet temperature being 50° C.

A2. Under identical spray conditions, a solution, at 25° C., of 33.4 parts of MSB, 1.6 parts of fumaric acid and 65 parts of water was sprayed into the fluidized bed. After sieving, the fraction of particles having a size of 125–250 μm was 55–56%.

A3. A solution, at 35° C., of 40 parts of MSB, 0.6 part of tartaric acid and 58.2 parts of water was sprayed as described in Example 1. A useful fraction of 125–250 μm particles was obtained, these particles accounting for from 60 to 80% of the content of the fluidized bed.
Shelf life The shelf life of the novel formulation was evaluated by a stress test. A premix composed of 70% of wheat bran, 20% of choline chloride (50% strength, SiO$_2$ carrier) and 10% of a trace element mixture and 0.1% of the novel formulation were stored in a conditioned chamber at 70% relative humidity and 40° C. After 1 week, samples were taken and the content of menadione still detectable was determined by the method described in USP XX.

The products from Examples A1.–A3. were subjected to the stability test described, under stress conditions.

The following residual contents of menadione, in percent, were found after a storage time of 1 week, the initial value being 100%.

| 1. | Product of Example A 1 | 78.4 |
| --- | --- | --- |
| 2. | Product of Example A 2 | 69.3 |
| 3. | Product of Example A 3 | 82.4 |
| 4. | Menadione sulfite dimethylpyrimidolium adduct | 49.1 |
| 5. | Menadione sulfite/nicotinamide adduct | 51.4 |
| 6. | MSB | 22.0 |

A4. A solution of 0.6 parts of tartaric acid, 65.4 parts of H$_2$O and 34 parts of MSB were sprayed continuously into a fluidized bed. Part of the initially taken solution was discharged continuously and classified. The useful fraction of 125–250 μm was isolated, and the milled oversize, together with the undersize and excess useful fraction, were recycled to the fluidized bed. The fluidizing gas was blown in at 85°–95° C. and emerged at 48°–55° C.

VARIANT B

Preparation Examples

B1. 100 parts of menadione sodium bisulfite, 20 parts of corn starch and 40 parts of gelatine, together with 20 parts of primary calcium phosphate, were dissolved in 600 parts of warm H$_2$O, and the solution was dried in a 1 cm thick layer in a drying oven at 40° C. under a reduced pressure of 25 mbar. The product was then crushed, and the stability determined as described below.

B2. A warm solution of 100 parts of menadione sodium bisulfite, 25 parts of citric acid and 75 parts of swellable corn starch were dried as described in Example 1. After crushing, a white powder having a residual moisture content of 6.4% and a menadione content of 25.1%, determined according to USP XX, page 473, was obtained.

B3. A suspension, at 50° C., of 100 parts of menadione sodium bisulfite, 20 parts of tartaric acid and 60 parts of swellable starch in 150 parts of water was atomized in the presence of hydrophobic silica via a nozzle and then dried in a fluidized bed at 28°–38° C. A very free-flowing dry powder having a menadione content of 29.5%, determinable according to USP XX, was obtained.

B4. A suspension, at 70° C., of 100 parts of menadione sodium bisulfite in the form of the bishydrate, 21.4 parts of sorbic acid and 57.1 parts of swellable starch in 150 parts of water was sprayed as described in Example B3. and dusted with 3.8 parts of hydrophobic silica gel. The dry powder had a residual moisture content of 6.5% and contained 30.4% of eliminable menadione.
Shelf life The shelf life of the menadione sodium bisulfite formulated according to variant B was evaluated by a stress test. A premix composed of 70% of wheat bran, 20% of choline chloride (50% strength, SiO$_2$ carrier, and 10% of a trace element mixture and 0.1% of the formulated menadione sodium bisulfite, based on the eliminable menadione content, were stored in a conditioned chamber at 70% relative humidity and 40° C. After 1 week, the amount of menadione still detectable was determined by the method described in USP XX, page 473.

Stabilities of the dry powders compared with the stabilized products Hetrazeen*, Kastab**) and commercial menadion sodium bisulfite without a stabilizer, after 1 week:

| Product according to Example | % of $K_3$ still detectable |
|---|---|
| 1 | 76 |
| 2 | 81 |
| 3 | 97 |
| 4 | 92 |
| *Menadione sulfite dimethylpyrimidolium adduct | 46 |
| **Menadione sulfite/nicotinamide adduct | 45 |
| Menadione sodium bisulfite, commercial MSB (not stabilized) | 21 |

We claim:

1. A stabilized powdered or granulated menadione sodium bisulfite animal feed additive formulation as obtained by drying a solution of from 90 to 99% by weight of menadione sodium bisulfate and from 1 to 10% by weight of a physiologically tolerated organic or inorganic acid.

2. The formulation of claim 1, wherein the solution is an aqueous solution and wherein the solution is spray dried by the fluidized bed method.

3. The formulation of claim 1, wherein the solution is an aqueous solution and wherein the solution is spray dried by the granulation method.

4. A stabilized powdered or granulated menadione sodium bisulfite formulation as obtained by drying a solution or suspension of from 50 to 80% by weight of menadione sodium bisulfite, from 1 to 20% by weight of a physiologically tolerated organic or inorganic acid and from 1 to 49% by weight of a thickener.

5. The formulation of claim 4, wherein the solution is an aqueous solution and wherein the solution is spray dried by the fluidized bed method.

6. The formulation of claim 4, wherein the solution is an aqueous solution and wherein the solution is spray dried by the granulation method.

7. The formulation of claim 1, wherein the acid is selected from the group consisting of fumaric acid, sorbic acid, citric acid, lactic acid, phosphoric acid, tartaric acid and primary calcium phosphate.

8. The formulation of claim 1, wherein the acid is tartaric acid.

9. The formulation of claim 4, wherein the acid is selected from the group consisting of fumaric acid, sorbic acid, citric acid, lactic acid, phosphoric acid, tartaric acid and primary calcium phosphate.

10. The formulation of claim 4, wherein the acid is tartaric acid.

11. A process for the production of stable powdery or granular menadione sodium bisulfite formulations which comprises: dissolving from 90 to 99% by weight of menadione sodium bisulfite and from 1 to 10% by weight of a physiologically tolerated organic or inorganic acid, the percentages in each case being based on the dry formulation, in water; and evaporating the water at an elevated temperature.

12. The process of claim 11, wherein the water is evaporated by spray-drying the solution by the fluidized bed method.

13. The process of claim 11, wherein the water is evaporated by spray-drying the solution by the granulation method.

14. A process for the production of stable menadione sodium bisulfite formulations, which comprises: dissolving 50 to 80% by weight of menadione sodium bisulfite, 1 to 20% by weight of a physiologically tolerated acid and 1 to 49% by weight of a thickening agent, the percentages in each case being based on total solids, in water; and evaporating the water at an elevated temperature.

15. The process of claim 14, wherein the water is evaporated by applying a thin layer of the solution on metal sheets.

16. The process of claim 14, wherein the water is evaporated by spraying and drying in a fluidized bed.

* * * * *